(12) United States Patent
Lietz

(10) Patent No.: US 6,251,604 B1
(45) Date of Patent: Jun. 26, 2001

(54) RANDOM MUTAGENESIS AND AMPLIFICATION OF NUCLEIC ACID

(75) Inventor: Eric Lietz, Santa Cruz, CA (US)

(73) Assignee: Genopsys, Inc., Santa Cruz, CA (US)

( * ) Notice: Subject to any disclaimer, the term of this patent is extended or adjusted under 35 U.S.C. 154(b) by 12 days.

(21) Appl. No.: 09/374,274

(22) Filed: Aug. 13, 1999

(51) Int. Cl.[7] ............... C12Q 1/68; C12P 19/34; C07K 1/00; C07K 14/00; A01H 1/00
(52) U.S. Cl. ........... 435/6; 435/91.1; 435/172.1; 435/172.3; 530/350; 800/205
(58) Field of Search ......... 435/6, 172.1, 172.3; 800/205; 530/350

(56) References Cited

U.S. PATENT DOCUMENTS

| | | | |
|---|---|---|---|
| 4,959,312 | * | 9/1990 | Sirotkin ............... 435/91 |
| 5,668,294 | * | 9/1997 | Meagher et al. ........ 800/205 |
| 5,811,238 | * | 9/1998 | Stemmer et al. ........ 435/6 |
| 5,942,664 | * | 8/1999 | Baum et al. ........... 800/302 |

FOREIGN PATENT DOCUMENTS

| | | | |
|---|---|---|---|
| 0 466 083 A2 | 1/1992 | (EP) | C12N/15/10 |
| WO 91/15581 | 10/1991 | (WO) | C12N/15/10 |
| WO 98/42832 | 1/1998 | (WO) | C12N/15/09 |
| WO 00/24932 | 4/2000 | (WO) | C12Q/1/68 |

OTHER PUBLICATIONS

Young–Sharp, D. et al., "Site–Directed Mutagenesis Using Three Primers and Diagnostic RFLPs in a Single-Step Polymerase Chain Reaction", *Technique –A Journal of Methods in Cell and Molecular Biology*, vol. 2, No. 3, Jun. 1990, pp. 155–162.

Ito, W. et al., "A general method for introducing a series of mutations into cloned DNA using the polymerase chain reaction", *Gene*, vol. 102, No. 1 (1991), pp. 67–70.

Drutsa, V. et al., "Efficient Method for Site–Directed Mutagenesis of Plasmids and Cloning of Single–Stranded DNA Fragments", abstract from database BIOSIS (Biosciences Information Service) online, (1991), published in *Bioorganicheskaya Khimiya*, vol. 17, No. 11 (1991), pp. 1487–1493.

Ling, M. et al., "Approaches to DNA Mutagenesis: An Overview", *Analytical Biochemistry*, vol. 254, No. 2, Dec. 1997, pp. 157–178.

Landt, O., et al., "A general method for rapid site–directed mutagenesis using the polymerase chain reaction", *Gene*, vol. 96 (1990), pp. 125–128.

Horton, R. et al., "Engineering hybrid genes without the use of restriction enzymes: gene splicing by overlap extension", *Gene*, vol. 77 (1989), pp. 61–68.

Ge, L. et al., "Simultaneous Introduction of Multiple Mutations Using Overlap Extension PCR", *BioTechniques*, vol. 22, No. 1, Jan. 1997, pp. 28–30.

Joyce, G. et al., "A novel technique for the rapid preparation of mutant RNAs", *Nucleic Acids Res.*, vol. 17, No. 2, Jan. 1989, pp. 711–722.

Oliphant, A. et al., "An efficient method for generating proteins with altered enzymatic properties: Applications to β–lactamase", *Proc. Natl. Acad. Sci. USA*, vol. 86, No. 23, Dec. 1989, pp. 9094–9098.

* cited by examiner

Primary Examiner—Jeffrey Fredman
Assistant Examiner—Arun Chakrabarti
(74) Attorney, Agent, or Firm—Wilson Sonsini Goodrich & Rosati

(57) ABSTRACT

A method is provided for mutagenizing nucleic acids and proteins relative to an initial target nucleic acid sequence by the insertion, deletion, or substitution of one or more oligonucleotides during amplification.

27 Claims, 5 Drawing Sheets

SEQUENCE LISTING

<160> NUMBER OF SEQ ID NOS: 2

<210> SEQ ID NO: 1
<211> LENGTH: 51
<212> TYPE: DNA
<213> ORGANISM: Artificial Sequence
<220> FEATURE:
<223> OTHER INFORMATION: Description of Artificial Sequence: 5'-Primer

<400> SEQUENCE: 1
ctttaagaag gagatataca tatgtcgcaa cctgccgaga agaatgaaaa g            51

<210> SEQ ID NO: 2
<211> LENGTH: 49
<212> TYPE: DNA
<213> ORGANISM: Artificial Sequence
<220> FEATURE:
<223> OTHER INFORMATION: Description of Artificial Sequence: 3'-Primer

<400> SEQUENCE: 2
gatatgagct tgatcaccaa gtgactctat ttatttattt gccgttcat              49

US 6,251,604 B1

RANDOM MUTAGENESIS AND AMPLIFICATION OF NUCLEIC ACID

FIELD OF THE INVENTION

The present invention relates to methods for mutagenizing nucleic acids and proteins. More particularly, the present invention relates to methods for mutagenizing nucleic acids and proteins relative to an initial target nucleic acid sequence by the insertion, deletion, or substitution of one or more oligonucleotides during amplification.

BACKGROUND OF THE INVENTION

The sequences of genes encoding many important proteins have been determined at a rapid speed owing to the fast progress in the field of genomics. The three-dimensional structures of thousands of proteins have been determined by X-ray crystallography and other biophysical and biochemical methods, and many more polypeptide sequences critical for the biological function of the proteins have also been determined. However, to a large extent, the correlation between protein primary sequence, tertiary structure, and biological function remains elusive.

Proteins can generally tolerate a certain level of amino acid substitutions without severe consequences on folding or stability (Axe et al., (1996) Proch. Natl. Acad. Sci. U S A 93:5590–5594; Bowie et al., (1990) Science 247:1306–1310; Gassner et al. (1996) Proc. Natl. Acad. Sci. U S A 93:12155–12158; Baldisseri et al. (1991) Biochem. 30:3628–33; Huang et al. (1996) J. Mol. Biol. 258:688–703.; Rennel et al. (1991) J. Mol. Biol. 222:67–88; Shortle (1995) Curr. Opin. Biotechnol. 6:387–393). On the other hand, for many proteins, a single particular residue can be either critical to function and/or stability (Philippon et al. (1998) Cell Mol. Life Sci. 54:341–346). Although it is desirable to be able to predict protein folding pattern from its primary sequence and to correlate its structure with function in vivo, in reality, this has proven to be a formidable task.

One approach to studying protein structure and function is site-directed mutagenesis. It is an important, but cumbersome approach to compiling an overall picture of protein functional character, let alone stability and regulatory characteristics in vivo. For example, serine beta-lactamases have been found to exhibit very diverse primary structures and catalytic profiles, but almost all of the known three-dimensional structures for serine beta-lactamases exhibit a high degree of similarity with apparently equivalent chemical functionalities in the same strategic positions (Philippon et al. (1998) Cell Mol. Life Sci. 54:341–346).

The apparent complexity of macromolecular structure-function correlation has made random mutagenesis an attractive approach to redesigning proteins. Many of the random mutagenesis methods developed so far are designed to introduce random base-pair substitutions.

Methods of saturation mutagenesis utilizing random or partially degenerate primers that incorporate restriction sites have been described (Hill et al. (1987) Methods Enzymol. 155:558–568; Reidhaar-Olson et al. (1991) Methods Enzymol. 208:564–586; Oliphant et al. (1986) Gene 44:177–183).

Error-prone polymerase chain reaction is another methodology for randomly mutating genes by altering the concentrations of respective dNTP's in the presence of dITP (Leung, S. et al. (1989) Nucleic Acid Res. 17:1177–1195); Caldwell and Joyce (1992) In PCR Methods Application 2:28–33; Spee et al. (1993) Nucleic Acid Res. 21: 777–778).

"Cassette" mutagenesis is another method for creating libraries of mutant proteins (Huebner et al. (1988) Gene 73:319–325; Hill et al. (1987) Methods Enzymol. 155:558–568; Shiraishi and Shimura (1988) Gene 64:313–319; U.S. Pat. Nos. 5,830,720; 5,830,721; 5,830,722; 5,830,728; 5,830,740; 5,830,741; and 5,830,742). Cassette mutagenesis typically replaces a sequence block length of a template with a partially randomized sequence. The maximum information content that can be obtained is thus limited statistically to the number of random sequences in the randomized portion of the cassette.

A protocol has also been developed by which synthesis of an oligonucleotide is "doped" with non-native phosphoramidites, resulting in randomization of the gene section targeted for random mutagenesis (Wang and Hoover (1997) J. Bacteriol. 179: 5812–5819). This method allows control of position selection, while retaining a random substitution rate.

Zaccolo and Gherardi (1999) describe a method of random mutagenesis utilizing pyrimidine and purine nucleoside analogs (Zaccolo and Gherardi (1999) J. Mol. Biol. 285: 775–783). This method was successful in achieving substitution mutations which rendered a β-lactamase with an increased catalytic rate against the cephalosporin cefotaxime. Crea describes a "walk through" method, wherein a predetermined amino acid is introduced into a targeted sequence at pre-selected positions (U.S. Pat. No. 5,798,208).

Methods for mutating a target gene by insertion and/or deletion mutations have also been developed. It has been demonstrated that insertion mutations could be accommodated in the interior of staphylococcal nuclease (Keefe et al. (1994) Protein Sci. 3:391–401). Another insertional mutagenesis method involves a partial fragmentation by a high frequency cutting restriction endonuclease, phosphatasing, and circularizing by appropriate linkers (Fitzgerald et al. (1994) Protein Sci. 3:391–401). Examples of deletional mutagenesis methods developed include the utilization of an exonuclease (such as exonuclease III or Bal31) or through oligonucleotide directed deletions incorporating point deletions (Ner et al. (1989) Nucleic Acids Res. 17:4015–4023).

Methods have also been developed to create molecular libraries as a part of the process of engineering the evolution of molecules with desired characteristics. Termed "directed evolution" or some variant thereof, protocols describing this type of technology typically involve the reassembly of fragments of DNA, representing a "shuffled" pool; in effect, accelerating the recombinatorial process that leads to molecules with desired and/or enhanced characteristics (Stemmer (1994) Nature 370: 389–391; Zhang et al. (1997) Proc. Natl. Acad. Sci. 94: 4504–4509). Such "directed molecular evolution" approaches have been utilized to mutagenize enzymes (Gulik &Fahl (1995) Proc. Natl. Acad. Sci. USA 92: 8140–8144; Stemmer (1994) Nature 370: 389–391; You & Arnold (1996) Protein Eng. 9:77–83; Zhang et al. (1997) Proc. Natl. Acad. Sci. USA. 94:4504–4509), antibodies (Barbas et al. (1994) Proc. Natl. Acad. Sci. USA. 91: 3809–3813; Crameri et al. (1997) Nature Biotech. 15:436–438.), fluorescent proteins (Heim & Tsien (1996) Curr. Biol. 6:178–182.; Siemering et al. (1996) Curr. Biol. 6:1653–1663). and entire operons (Crameri et al. (1996) Nature Med. 2: 100–102).

SUMMARY OF THE INVENTION

The present invention provides methods of random mutagenesis which facilitate random insertions and deletions on a target polynucleotide with random-sequenced oligonucleotides. The methods can be used to generate random libraries of polynucleotides and polypeptides and search within the libraries the polynucleotides or the polypeptides with desired biological characteristics under specified environment.

In one embodiment, a method is provided for producing mutagenized polynucleotides from a target sequence, comprising:
(a) forming a sample comprising
    (i) a target sequence including a section to be mutagenized,
    (ii) a first primer including a sequence complementary to a 3' sequence of a sense strand of the section of the target sequence,
    (iii) a second primer including a sequence complementary to a 3' sequence of an antisense strand of the section of the target sequence, and
    (iv) at least one oligonucleotide;
(b) performing at least one cycle of primer extension amplification on the sample in the presence of at least one polymerase such that the oligonucleotide anneals to either the sense or antisense strand of the section of the target sequence to form an imperfect double-stranded sequence and is extended by the polymerase; and
(c) performing additional cycles of primer extension amplification on the sample to form a mutagenized double-stranded polynucleotide comprising sequences of the first and second primers and the sequence of the oligonucleotide extended in step (b).

According to the above method, the at least one oligonucleotide may optionally include a portion which is complementary to the target sequence and a portion which is not complementary to the target sequence relative to where the oligonucleotide anneals to the target sequence during primer extension amplification, the portion which is not complementary to the target sequence being unknown at the time of primer extension amplification.

Also according to the above method, the at least one oligonucleotide may have a sequence which is unknown at the time of primer extension amplification.

Also according to the above method, a portion of the target sequence to which the at least one oligonucleotide anneals during primer extension amplification may be unknown at the time of primer extension amplification.

In another embodiment, a method is provided for producing mutagenized polynucleotides from a target sequence comprising:
forming a sample comprising:
    (i) a target sequence including a section to be mutagenized,
    (ii) a first primer including a sequence complementary to a 3' sequence of a sense strand of the section of the target sequence,
    (iii) a second primer including a sequence complementary to a 3' sequence of an antisense strand of the section of the target sequence, and
    (iv) a library of oligonucleotides; and
performing multiple cycles of primer extension amplification on the sample using a polymerase where primer extension is performed under conditions suitable for the oligonucleotides to anneal to the section of the target sequence or amplification products thereof to form imperfect double-stranded sequences and be extended by the polymerase;
wherein a library of mutagenized polynucleotides are produced as amplification products of the multiple amplification cycles.

According to the above method, the oligonucleotides in the library of oligonucleotides may optionally include a portion which is complementary to the target sequence and a portion which is not complementary to the target sequence relative to where the oligonucleotide anneals to the target sequence during primer extension amplification, the portion which is not complementary to the target sequence being unknown at the time of primer extension amplification.

Also according to the above method, the oligonucleotides in the library of oligonucleotides may have sequences which are unknown at the time of primer extension amplification.

Also according to the above method, portions of the target sequence to which the oligonucleotides in the library of oligonucleotides anneal during primer extension amplification may be unknown at the time of primer extension amplification.

In yet another embodiment, a method is provided for producing mutagenized polynucleotides from a double-stranded target sequence comprising:
(a) forming a sample comprising
    (i) a target sequence having sense and antisense strands and including a section to be mutagenized,
    (ii) a first primer including a sequence complementary to a 3' sequence of the section of the sense strand of the target sequence,
    (iii) a second primer including a sequence complementary to a 3' sequence of the section of the antisense strand of the target sequence, and
    (iv) a library of oligonucleotides;
(b) performing at least one cycle of primer extension amplification on the sample in the presence of at least one polymerase such that at least one of the oligonucleotides anneals to either the sense or antisense strand of the section of the target sequence to form an imperfect double-stranded sequence and is extended by the polymerase; and
(c) performing additional cycles of primer extension amplification on the sample to form mutagenized double-stranded polynucleotides comprising sequences of the first and second primers and the at least one oligonucleotides extended in step (b).

According to the above method, the oligonucleotides in the library of oligonucleotides may optionally include a portion which is complementary to the target sequence and a portion which is not complementary to the target sequence relative to where the oligonucleotide anneals to the target sequence during primer extension amplification, the portion which is not complementary to the target sequence being unknown at the time of primer extension amplification.

Also according to the above method, the oligonucleotides in the library of oligonucleotides may have sequences which are unknown at the time of primer extension amplification.

Also according to the above method, portions of the target sequence to which the oligonucleotides in the library of oligonucleotides anneal during primer extension amplification may be unknown at the time of primer extension amplification.

Methods are also provided for producing mutagenized polypeptides from a target sequence by forming a library of mutagenized polynucleotides according to any of the above methods and expressing polypeptides from the library of mutagenized polynucleotides.

According to any of the above methods, the target sequence may have a sequence which is known or partially or completely unknown.

Also according to any of the above methods, the first and second primers preferably include at least one restriction site, respectively, which facilitates subcloning in an expression vector, and the ultimate synthesis of polypeptides from the polynucleotides produced according to the methods.

Also according to any of the above methods, one of the first and second primers may include a "start" codon sequence (e.g. ATG or GTA) and the other primer may include a sequence encoding one or more translation stop codons.

Also according to any of the above methods, the lengths of the first and second primers may optionally be between 10 and 80 nucleotides, preferably between 12 and 60 nucleotides and more preferably between 15 and 40 nucleotides.

Also according to any of the above methods, sequences of the oligonucleotides are preferably partially or completely unknown. It is noted, however, that the sequences of some of the oligonucleotides may be known prior to amplification.

The library of oligonucleotides may optionally be synthetic and may be synthesized by randomly incorporating A, T, G, C, I or U.

At least some of the oligonucleotides used in the library of oligonucleotides in the above methods preferably have a length between 3 and 100 nucleotides, preferably between 10 and 80 nucleotides, more preferably between 10 and 50 nucleotides, and most preferably between 15–30 nucleotides.

Also according to any of the above methods, the sample formed preferably includes first and second primers at a concentration approximately equivalent to the concentration of the oligonucleotides. The concentration of the oligonucleotide is preferably between about 0.1 $\mu M$ to 10 $\mu M$, more preferably between about 0.1 $\mu M$ to 5 $\mu M$, and most preferably between about 0.5 $\mu M$ to 1 $\mu M$,.

Also according to any of the above methods, the sample formed preferably includes salts such as NaCl and $Mg^{2+}$.

Also according to any of the above methods, at least a portion of the multiple cycles of primer extension polymerase amplification may be performed such that extension by the polymerase is at least partially performed at a temperature below 70° C. for at least 30 sec.

Also according to any of the above methods, at least a portion of the multiple cycles of primer extension polymerase amplification may be performed such that extension by the polymerase is at least partially performed at a temperature below 60° C. for at least 30 sec.

Also according to any of the above methods, at least a portion of the multiple cycles of primer extension polymerase amplification may be performed such that extension by the polymerase is at least partially performed at a temperature below 50° C. for at least 30 sec.

Also according to any of the above methods, at least a portion of the multiple cycles of primer extension polymerase amplification may be performed such that extension by the polymerase is performed by heating the amplification reaction mixture from a temperature between about 30° C. to 50° C. to a temperature between about 65° C. to 75° C. for at least 30 sec.

Also according to any of the above methods, at least a portion of the multiple cycles of primer extension polymerase amplification may be performed by ramping the temperature about 30° C. to 50° C. to a temperature between about 65° C. to 75° C. for at least 1 min.

Also according to any of the above methods, at least a portion of the multiple cycles of primer extension polymerase amplification may be performed by ramping the temperature about 30° C. to 50° C. to a temperature between about 65° C. to 75° C. for at least 1 min, wherein the incubation time after each ramp is shorter than that of the previous ramp.

Also according to any of the above methods, it is noted that the imperfect double-stranded sequence formed during the at least one cycle of primer extension amplification may include mismatches, bulges or loops.

Also according to any of the above methods, it is noted that the library of mutagenized polynucleotides formed may include homologs of the target sequence where at least two sequences from the oligonucleotides have been inserted.

Also according to any of the above methods, it is noted that the library of mutagenized polynucleotides formed may include homologs of the target sequence where at least two portions of the target sequence have been deleted.

Also according to any of the above methods, it is noted that the library of mutagenized polynucleotides formed may include homologs of the target sequence where at least a portion of the mutagenized polynucleotides have been mutagenized at at least two separate locations on the target sequence.

BRIEF DESCRIPTION OF THE FIGURES

FIG. 3A illustrates a temperature profile where after the denaturation of the mixture, the oligonucleotides are allowed to anneal to the target at a sufficiently low temperature and the annealing temperature is then gradually raised until reaching the optimum temperature for the polymerase.

FIG. 3B illustrates a temperature profile where the annealing temperature is raised by combining gradual rise with ramping.

FIG. 3C. illustrates a temperature profile where the annealing temperature is raised by several ramps or in a step-wise manner where the incubation time after each ramp/step is shorter than previous one.

DETAILED DESCRIPTION OF THE INVENTION

Figure 1:
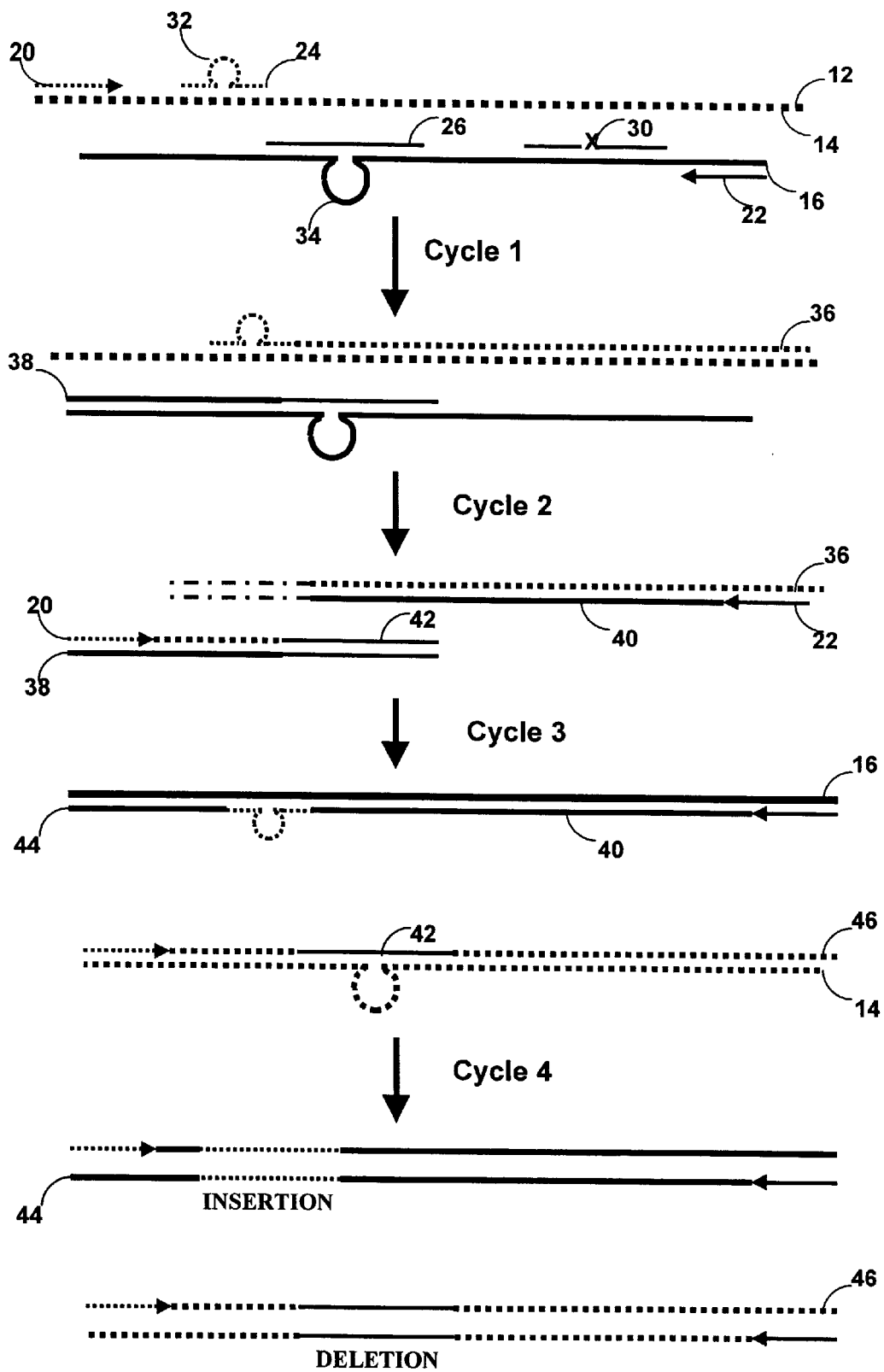
FIG. 1 schematically illustrates mutagenesis of a gene sequence (target sequence) using oligonucleotides which result in insertion, deletion and substitution of the gene sequence.

The present invention provides methods for generating a library of mutagenized polynucleotides from a target sequence. Any gene sequence can serve as the target sequence and be mutagenized according to the methods of the present invention to yield a large and diverse population of mutagenized polynucleotides having some degree of homology to the target sequence. These polynucleotides can then be subcloned into expression vectors to produce proteins with diverse structures, biophysical stabilities, and biological functions relative to the protein encoded by the target sequence.

According to the present invention, multiple cycles of primer extension amplification are performed on a sample including the template target sequence to be mutagenized; a first primer including a sequence complementary to a 3' sequence of a sense strand of the section of the target sequence; a second primer including a sequence complementary to a 3' sequence of an antisense strand of the section of the target sequence; and one or more oligonucleotides which are not perfectly complementary to the target sequence relative to where the oligonucleotide anneals to the target sequence during primer extension amplification.

Amplification is conducted under conditions such that the one or more oligonucleotides form an imperfect double-stranded sequence with the target sequence during amplification and are extended. The imperfect double-stranded sequence formed with the target sequence during amplification can include mismatches, bulges or loops in the primer and/or template target sequence. After multiple amplification cycles, the extended oligonucleotide forms an amplification product which is a homolog of the target sequence where all or a portion of the sequence of the oligonucleotide has been introduced into the target sequence. Depending on the imperfect double-stranded sequence formed, the amplification product may correspond to an insertion, deletion or substitution of a portion or portions of the target sequence.

A feature of the present invention is that one need not know the sequences of the one or more oligonucleotides used in the method. Rather, all or a portion of the sequences of the one or more oligonucleotides may be unknown at the time of primer extension amplification. By being able to use oligonucleotides where all or a portion of their sequences are unknown at the time of primer extension amplification, for example by using random sequences, it is possible to conduct amplifications which are less carefully controlled. This allows random libraries of sequences to be used as the one or more oligonucleotides and obviates the need to custom design the oligonucleotides relative to the target sequence. Since the range of oligonucleotides that may be used is not limited by one's ability to custom synthesize particular sequences, the sequence space and molecular diversity of the resulting library of mutagenized polynucleotides and polypeptides is significantly enlarged.

A further feature of the present invention is that one need not know the location where the one or more oligonucleotides anneal to the target sequence during amplification. Instead, the oligonucleotides may form base pairs with the target gene sequence wherever is suitable under the amplification conditions. This departure from a controlled mutagenesis approach allows the range of oligonucleotides that may be used to be significantly increased beyond what one can custom synthesize, simplifies the planning and time required to create the mutagenized polynucleotides, and ultimately increases the molecular diversity of the resulting library of mutagenized polynucleotides and polypeptides.

Yet a further feature of the present invention is that multiple oligonucleotides can be incorporated into the target sequence. This results in further enhanced heterology between the mutagenized polynucleotides and the original target gene.

Yet a further feature of the present invention is that different libraries of mutagenized polynucleotides can be generated from the same group of oligonucleotides. The one or more oligonucleotides anneal to the target sequence at locations which depend upon the homology of a particular oligonucleotide to a given section of the target sequence and the conditions of the amplification. By varying the amplification conditions (such as annealing temperature, salt concentration, or other factors), different oligonucleotides anneal to the target sequence, in different ways, and at different locations. These different forms of annealing control what insertions, deletions, or changes (substitutions or point mutations) in the target sequence occur during the amplification cycles. As a result, one is able to vary and control the degree of random incorporated mutations such as insertion, deletion, and substitution by controlling the amplification conditions and achieve different degrees of mutagenicity.

According to one embodiment of the method, a sample is formed which comprises (i) a target sequence including a section to be mutagenized, (ii) a first primer including a sequence complementary to a 3' sequence of a sense strand of the section of the target sequence, (iii) a second primer including a sequence complementary to a 3' sequence of an antisense strand of the section of the target sequence, and (iv) at least one oligonucleotide. At least one cycle of primer extension amplification is performed on the sample in the presence of at least one polymerase such that the at least one oligonucleotide anneals to either the sense or antisense strand of the target sequence to form an imperfect double-stranded sequence and is extended by the polymerase. Additional cycles of primer extension amplification are then performed on the sample to form mutagenized double-stranded polynucleotides comprising sequences of the first and second primers and the oligonucleotides which are extended by the polymerase. The mutagenized double-stranded polynucleotides formed during the method can differ from the target sequence in one or more locations and can include insertions, deletions, and/or substitutions of one or more oligonucleotides.

The above embodiment may be extended to where a library of oligonucleotides are employed. For example, a method is also provided which includes forming a sample comprising (i) a target sequence including a section to be mutagenized, (ii) a first primer including a sequence complementary to a 3' sequence of a sense strand of the section of the target sequence, (iii) a second primer including a sequence complementary to a 3' sequence of an antisense strand of the section of the target sequence, and (iv) a library of oligonucleotides. Multiple cycles of primer extension amplification are performed on the sample using a polymerase where primer extension is performed under conditions suitable for the oligonucleotides to anneal to the target sequence or amplification products thereof to form imperfect double-stranded sequences and be extended by the polymerase. As a result of the multiple amplification cycles, a library of mutagenized polynucleotides are produced as amplification products where the one or more oligonucleotides are incorporated into the target sequence at one or more locations. These incorporations cause mutations such as insertions, deletions, and substitutions in one or more locations on the target sequence.

As noted above, one need not know the sequence of the oligonucleotides used in the method or where and how the oligonucleotides anneal to the target sequence during amplification. In that regard, it is also not necessary to know the sequence of the target sequence prior to performing the method, aside from the portions of the target sequence to which the first and second primers anneal.

Once the mutagenized polynucleotides are generated by the above-described methods, the mutagenized polynucleotides can be further subcloned into suitable expression vectors after restriction digestion or direct cloning of PCR products. The proteins encoded by the mutagenized polynucleotides can be expressed in prokaryotic or eukaryotic expression systems. The biological functions of the expressed proteins can then be screened and proteins with altered, preferably improved, biological activity selected. Thus, the present invention provides powerful tools for generating large libraries of polynucleotides and their corresponding polypeptides, which can be screened for diverse structures and functions.

Unlike cassette mutagenesis where a sequence block of a single template is typically replaced by a partially randomized sequence, the present invention enables one to generate a library of mutagenized polynucleotides where the sequence of the target sequence has been altered at multiple locations, thus generating a much larger and more diverse library of randomized sequences. In addition, by using the first and second primers that are designed to incorporate desired restriction sites, translation start or stop codons, and to have complementary sequences flanking the section to be mutagenized, the resulted library of mutagenized oligonucleotides can be efficiently subcloned into expression vectors and a library of polypeptides encoded by the mutagenized target sequences can be expressed.

The synthesis of a large library of polynucleotides relative to the target sequence has a wide variety of applications. For example, the mutagenized polynucleotides can be used to screen for novel nucleic acid (DNA or RNA) therapeutics that can act as ligands for a protein such as aptamers, or for novel ribozymes that can act as efficient enzymes for various substrates. Viral genes encoding critical regulatory proteins can be mutagenized and screened for transdominant inhibitors that can be developed into more specific and efficacious antiviral therapeutics such as gene therapy. Viral genome can also be mutagenized and screened for more potent viral vaccines such as DNA vaccines.

Further, the proteins encoded by the library of mutagenized target sequences can be screened for various novel functions or optimized functions. For example, genes encoding important enzymes can be mutagenized and the corresponding expressed proteins can be screened for novel binding affinity to a target molecule, and for improved catalytic activity, thermal stability, substrate specificity, ligand binding affinity, etc.

For industrial enzymes, environmental conditions may be radically different from the physiological or native environment, some of which may seem to be too harsh for the normal function of native enzymes, such as high temperature and alkalinity. By using the methods of the present invention, a target enzyme may be extensively and dramatically mutated in order to identify homologs of the protein which have superior thermal stability or resistance to harsh environmental elements.

Therapeutic antibodies, cytokines and growth factors can also be mutagenized and screened for improved shelf stability, pharmacokinetics, higher in vivo activity, and reduced side effects. Genomes of microorganisms can be mutagenized and screened for industry applications such as chemical and drug processing, oil spill clean-ups and pollution treatment.

The present invention will now be described in relation to the figures. FIG. 1 illustrates an embodiment in which a sample is formed which includes a target sequence 12 having sense 14 and antisense 16 strands. Also included in the sample is a first primer 20 including a sequence complementary to a 3' sequence of the section of the sense strand 14 of the target sequence 12, a second primer 22 including a sequence complementary to a 3' sequence of the section of the antisense strand 16 of the target sequence 12, and a first oligonucleotide 24 and a second oligonucleotide 26. It is noted that the first and second oligonucleotides 24, 26 are used here to illustrate an insertion and a deletion respectively. These first and second oligonucleotides 24, 26 may be employed separately, together as illustrated, and may be part of a broader library of oligonucleotides.

After forming the sample, the sample is heated to a temperature which is sufficiently high to denature all the sequences in the sample (e.g. about 95° C.). The sample is then cooled, typically to a temperature below 50° C. Upon cooling, the primers 20, 22 and the first and second oligonucleotides 24, 26 anneal to the target sequence. As illustrated, the first and second oligonucleotides 24, 26 are not perfectly complementary to the target sequence and form imperfect double-stranded sequences including mismatches 30, bulges 32 and internal loops 34. When incubated in the presence of at least one polymerase (e.g. a thermal stable polymerase such as Taq), the first and second oligonucleotides 24, 26 are extended along the target sequence to form extended sequences 36, 38 respectively.

During Cycle 2, complements 40, 42 of extended sequences 36, 38 are formed. It is noted that the complement 40 of extended sequence 36 includes the sequence of the second primer 22 and complement 42 of extended sequence 38 includes the sequence of the first primer 20.

During Cycle 3, complements 40, 42 are extended using the sense 14 and antisense 16 strands of the target sequence 12 as templates to form mutant complements 44, 46 of the sense 14 and antisense 16 strands of the target sequence 12. Alternatively, strands 40 and 42 may be extended by forming mutant complements with the randomized products.

During Cycle 4, duplexes of mutant complements 44, 46 are formed using the first and second primers 20, 22. As illustrated, the bulge 32 formed by the first oligonucleotide 24 results in mutant complement 44 being an insertion relative to the target sequence 12. Meanwhile, the internal loop 34 formed by the second oligonucleotide 26 results in mutant complement 46 being a deletion relative to the target sequence 12. It is noted that an oligonucleotide may also cause a substitution relative to the target sequence 12 when neither a bulge or an internal loop is formed.

While the first and second oligonucleotides 24, 26 are shown annealing to the target sequence at single locations, it is noted that the first and second oligonucleotides 24, 26 may anneal to the denatured strands of the target sequence at different positions along the strand depending on the amplificaiton conditions. For example, at lower annealing temperatures, the oligonucleotides need be less complementary to the target sequence to anneal.

It is further noted that different sets of oligonucleotides may anneal to the target sequence depending on the amplification conditions. For example, at one temperature, a first set of oligonucleotides anneal while at a second, lower temperature, a broader range of oligonucleotides anneal to the target sequence.

Figure 2:
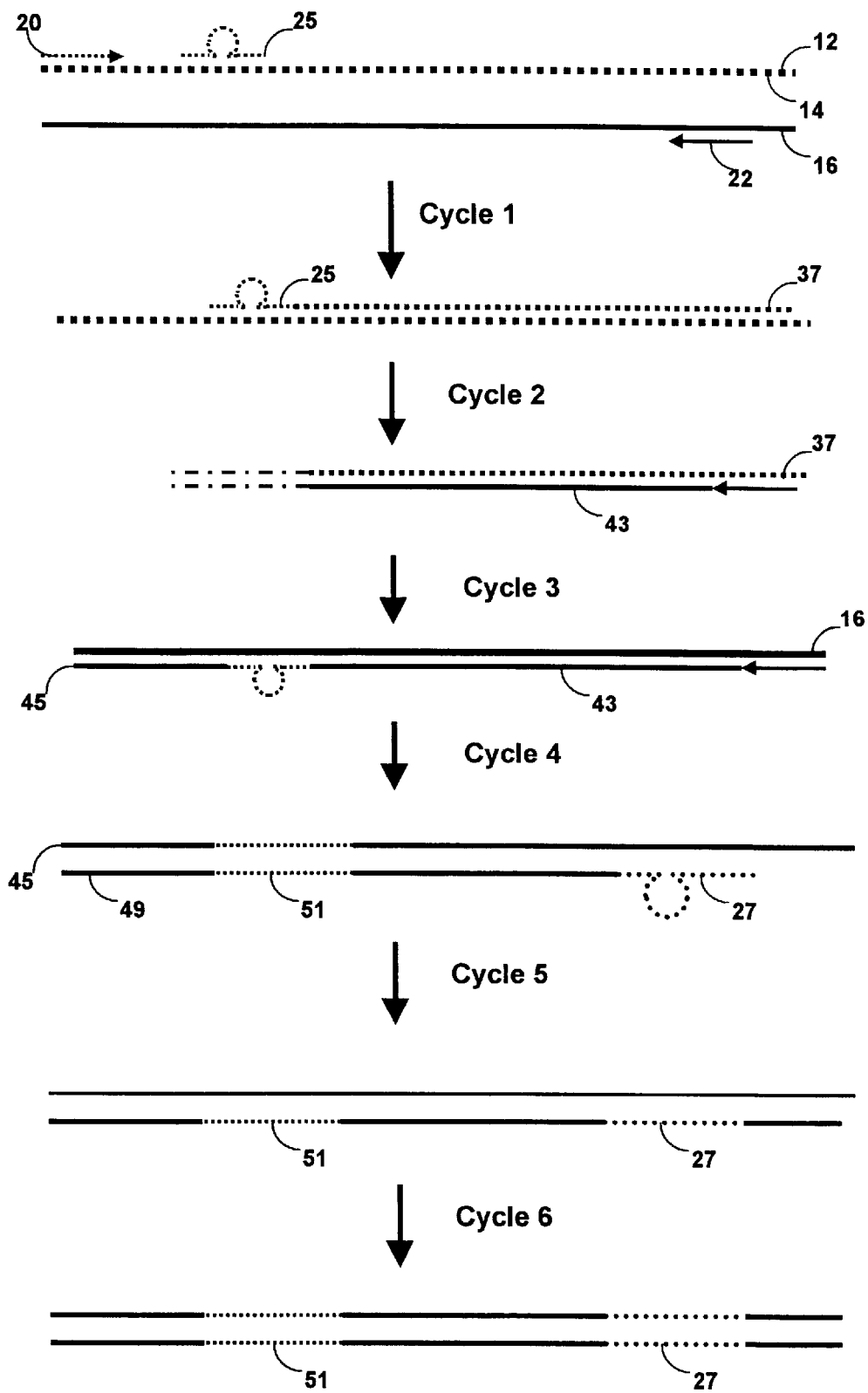
FIG. 2 illustrates an embodiment where two oligonucleotides are used to mutate the target sequence at two separate locations.

FIG. 2 illustrates an embodiment where two oligonucleotides are used to mutate the target sequence at two separate locations. As illustrated, a sample is formed which includes a target sequence 12 having sense 14 and antisense 16 strands. Also included in the sample is a first primer 20 including a sequence complementary to a 3' sequence of the section of the sense strand 14 of the target sequence 12, a second primer 22 including a sequence complementary to a 3' sequence of the section of the antisense strand 16 of the target sequence 12, and a first oligonucleotide 25 and a second oligonucleotide 27.

After forming the sample, the sample is heated to a temperature which is sufficiently high to denature all the sequences in the sample (e.g. about 95° C). The sample is then cooled, typically to a temperature below 50° C. Upon cooling, the first oligonucleotide 25 anneals to the target sequence. As illustrated, the first oligonucleotide 25 is not perfectly complementary to the target sequence and forms an imperfect double-stranded sequence. When incubated in the presence of at least one polymerase (e.g. a thermal stable polymerase such as Taq), the first oligonucleotide 25 is extended along the target sequence to form extended sequence 37.

During Cycle 2, complement 41 of extended sequences 37 is formed. It is noted that the complement 41 of extended sequence 37 includes the sequence of the second primer 22.

During Cycle 3, complement 41 is extended using the antisense 16 strand of the target sequence 12 as a template to form a mutant complement 45.

During Cycle 4, the second oligonucleotide 27 anneals to the mutant complement 45 and is extended relative to the mutant complement 45. As illustrated, the mutant 49 formed includes the second oligonucleotide 27 and a complement 51 of the first oligonucleotide 25.

During Cycle 5, mutant 49 is extended relative to the target sequence to form mutant 52.

During Cycle 6, a duplex of mutant 52 is formed which includes first and second oligonucleotides 25, 27.

As can be seen from FIG. 2, a very wide array of polynucleotides can be generated depending on what oligonucleotides are present in the sample and the number of amplification cycles that are performed.

Once a library of mutagenized polynucleotides are formed, for example as illustrated in FIGS. 1 and 2, mutagenized polypeptides may be formed from the mutagenized polynucleotides. For example, the library of mutagenized polynucleotides may be cloned into an appropriate expression vector, and the resulting vector may be used to transform, transfect or transduce a host cell to produce the mutant proteins. The mutant proteins can then be screened for novel functionality or desired characteristics.

1. Target Sequence

The target sequence can be any sequence. For example, the target sequence can be a gene (either wild-type or mutant), a strand of synthetic DNA oligonucleotide, or an RNA from viruses or cellular extracts. The target sequence can be single- or double-stranded, present as linear nucleotides or residing in a section of a circularized plasmid. The sequence of the target sequence may be known or only partially known. Examples of target sequences with partially known sequences include a linear or circular target sequence that has sections of known sequences flanking an unknown sequence. The unknown sequence may be a full length or a truncated fragment of a gene and this gene may be mutagenized by using primers homologous to the flanking sections with known sequences.

Single-stranded mRNA or the RNA genomes of certain viruses can be converted to DNA by reaction with reverse transcriptase (RT). The product of the reverse transcriptase reaction may then be amplified by using polymerase chain reaction (RT-PCR) and used as a target sequence.

2. First and Second Primers

The first and second primers serve as upstream (5') and downstream (3') primers which flank the section of the target sequence to be mutagenized. The primers can be completely or partially complementary to the target sequence.

The primers may be modified with biotin or other detectable markers which may be desirable in the detection, quantification, isolation and purification of the amplification products.

The primers may also include at least one restriction site as well as a 'tail' composed of a number of bases; the number dictated by the restriction enzyme as required for efficient cleavage. Such sites would allow, for example, cloning of amplification products into a vector having the matching restriction sites. The primer may also include transcription promoter sequences (e.g. TATA boxes) or RNA polymerase terminator sequences to allow efficient transcription of the amplification products.

The upstream primer preferably includes a restriction site that incorporates an translational "start" codon, such as NdeI or NcoI. A NdeI site includes an ATG sequence and may be useful for subsequent subcloning and expression in Gram-negative bacterial hosts recognizing ATG as "start" codon. A NcoI site includes a GTA sequence and may be useful for subsequent subcloning and expression in Gram-positive bacterial hosts.

The downstream primer preferably includes a translational "stop" codon such as TM, TGA or TAG, in at least one, and preferably all three reading frames.

The length of the first and second primers should be of a sufficient length to prime the synthesis of extension products in the presence of a polymerase. The first and second primers are preferably between 10 and 80 nucleotides in length, more preferably between 15 and 60 nucleotides, and most preferably between 15 and 35 nucleotides.

The ratio of the concentration of the first primer to the concentration of the second primer in the sample can be used to control the mixture of mutagenized polynucleotides formed. For example, by using a higher concentration of the upstream primer relative to the downstream primer, the oligonucleotides will tend to mutate the end of the target sequence adjacent the downstream primer. Conversely, by using a higher concentration of the downstream primer relative to the upstream primer, the oligonucleotides will tend to mutate the end of the target sequence adjacent the upstream primer. Without being bound by theory, it is believed that mutation is favored adjacent the primer with the lower concentration due to the lower annealing efficiency of the oligonucleotides relative to the flanking primers because the oligonucleotides are less complementary.

3. Oligonucleotides

A key feature of the present invention is the ability to use oligonucleotides whose sequences are not completely known at the time of amplification. A portion of the oligonucleotide sequence may be known while another portion of the oligonucleotide sequence is unknown. Alternatively, the entire oligonucleotide sequence may be unknown at the time of amplification.

In the case of oligonucleotide libraries, the libraries can include oligonucleotides where only a portion of the oligonucleotide sequence is known and/or where none of the oligonucleotide sequence is known. For example, libraries where no sequences are known can be created by a complete randomization method by chemically synthesizing the library by mixing different phosphoramidites at a substantially equal ratio (e.g. A:T:C:G=25%:25%:25%:25%). Complete randomization of the library maximizes the molecular diversity for an oligonucleotide at a certain length (e.g. theoretical library size=$4^n$, n: length of the oligonucleotide).

Libraries where a portion of the sequences are known can be created by a partial randomization method by which oligonucleotides include at least one section of conserved/specified or known sequences and a section with a randomized sequence. The specified sequence may not be required to contain restriction nuclease sites. Oligonucleotides containing sections of conserved sequences may be designed to target specific regions of the target sequence, such as an active site of an enzyme or a ligand binding site of a protein, thereby causing more predominant mutagenesis in these regions.

Libraries can also be synthesized which have biased randomization. This can be achieved by synthesizing the oligonucleotide library with a mixture of a conserved base and other phosphoramidites doped into at lower percentages (e.g. below 25%). For example, the mixture may contain a higher percentage of a conserved base (e.g. A at 70%) and a much lower percentage of other bases (T, C. and G at 10%, respectively). Such biased randomization allows one to tune the mutagenecity of the target sequence, thereby producing libraries of oligonucleotides with different degrees of homology to the target sequence.

Oligonucleotide libraries can be synthesized by routine solid phase synthesis that incorporates naturally occurring bases such A, T, G, C, I or U, or unnatural bases that may not interfere with the primer extension by polymerase at each position (Barbas, C.F. et al. Angew. Chem. Int. Ed. (1998) 37: 2872–2875).

Oligonucleotide libraries may also be derived from random restriction digestion, non-site-specific nuclease fragmentation, or randomly shearing by sonication of DNA from various sources.

Oligonucleotide libraries derived by any of the above methodologies can also be modified in a variety of different manners prior to use. For example, it may be desirable to select from a library only those oligonucleotides which can anneal to the target sequence at selected stringency conditions. Those oligonucleotides which do not anneal to the target sequence under the selected stringency conditions may be discarded. This selection process may be used to increase the concentration of oligonucleotides in the library which can initially anneal to the target sequence. The selected stringency conditions may optionally be the initial conditions for the amplification.

The length of the oligonucleotides must be at least 3 nucleotides, preferably between 3 to 80 nucleotides, preferably between 10 and 80 nucleotides, more preferably between 10 and 60 nucleotides, more preferably between 10 and 40 nucleotides, and most preferably 15 and 30 nucleotides. It is contemplated that longer oligonucleotides may result in longer insertions and/or deletions. In a library of oligonucleotides, oligonucleotides can have uniform lengths or mixed lengths.

4. Amplification Conditions

The method according to the present invention can be used to tune the degree of mutagenesis of a target sequence. This is achieved by exploiting the structural versatility and dynamics of nucleic acids under different amplification conditions. Annealing and dissociation of an oligonucleotide to a target sequence may be dependent on many factors, such as temperature, pH, ionic strength, $Mg^{2+}$ concentration, etc. In general, heating or high pH (~12) would destabilize (or denature) intra- or inter-molecular base pairing, while lowering the temperature would favor the formation of duplexes (intermolecular interaction) and hairpins (intramolecular interaction). Under suitable conditions an oligonucleotide that is partially complementary to a target sequence may form an imperfect duplex which may contain mismatches, bulges and internal loops. Such duplexes may be stabilizd by lowering the temperature or adjusting ionic strength of the solution, i.e. under less stringent conditions. At lower temperature, dynamic breathing of the duplex may be significantly reduced. Therefore, in the presence of polymerase, extension of the oligonucleotide can be achieved even though the oligonucleotide is not completely complementary to the target sequence. A more detailed description of the methodology is described as follows.

The target sequence, first and second primers, and the one or more oligonucleotides can be mixed and denatured at suitable conditions known to one skilled in the art, such as by heating or by alkali treatment. For example, the mixture can be heated to between 85 to 100° C., more preferably between 90 to 95° C., most preferably at about 94° C.

Once denatured, the one or more oligonucleotides in the sample may be annealed to the target sequence by incubating the mixture under suitable conditions. For example, the sample may be incubated for at least 30 sec. at a temperature below 60° C., more preferably below 55° C., and most preferably below 50° C. The lowering of the temperature from denaturation to annealing may be performed in a ramped, stepwise, or linear manner. Incubation at these lower temperatures is believed to enhance the annealing of the oligonucleotides to the target sequence by stabilizing the imperfect double-stranded complex formed. At lower temperatures, less perfect double-stranded complex can be formed.

In the presence of at least one polymerase, the oligonucleotides annealed to the target sequence are extended. The sample is incubated in the presence of the polymerase for a sufficient period of time to allow full-length extension.

As the oligonucleotides are extended, the oligonucleotides become more complementary to the target sequence, thereby stabilizing the imperfect double-stranded complex formed between the oligonucleotides and the target sequence. As the oligonucleotides are extended, it is possible to gradually increase the temperature, preferably to 72° C. Increasing the temperature from below 55° C. to about 72° C. is desirable since TAQ polymerase activity increases to a maximum at around 72° C.

Figure 3:
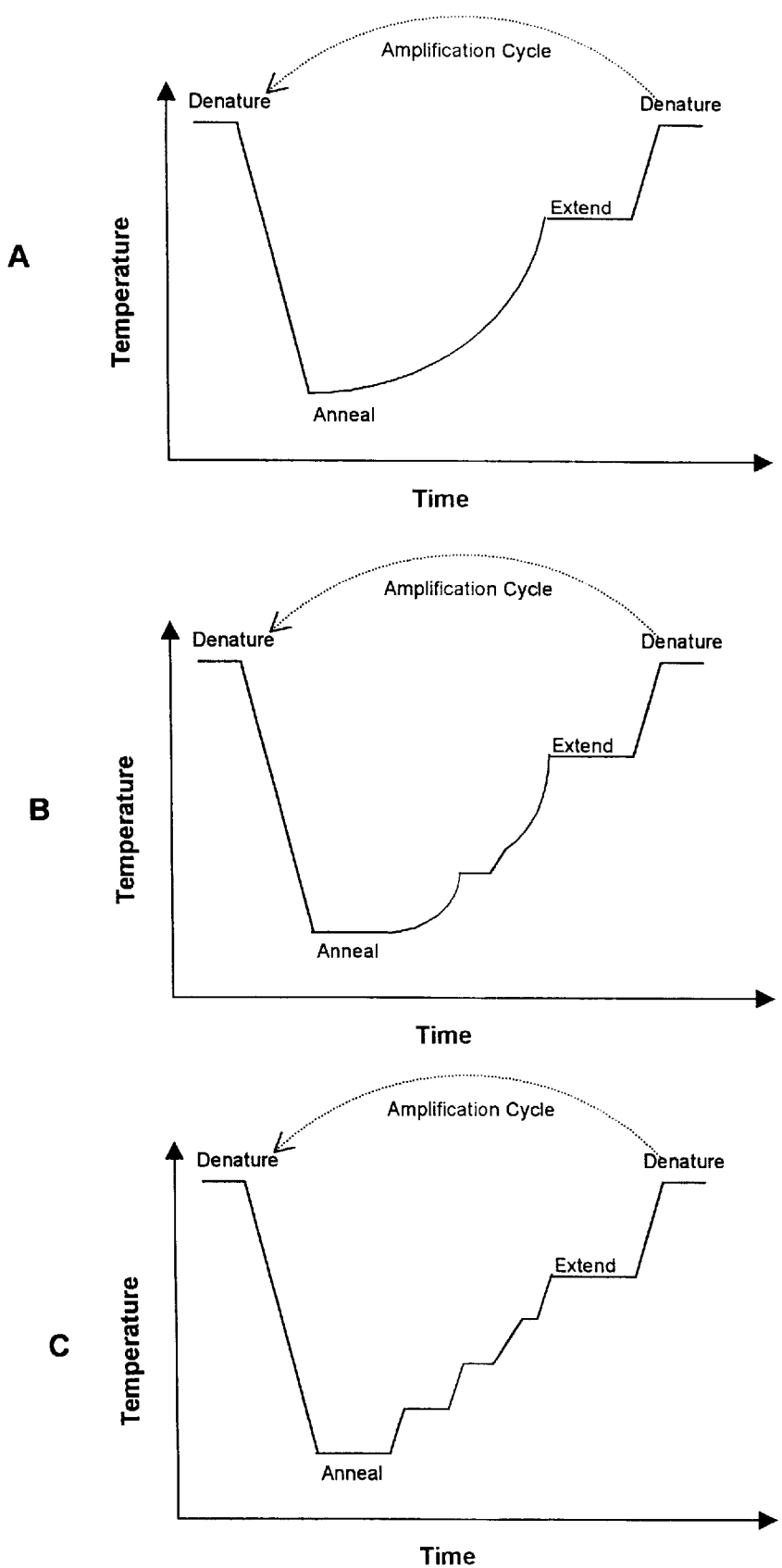
FIG. 3A–C. illustrate three examples of the temperature profiles that may be used in the method.

FIG. 3A–C. illustrate three temperature profiles that may be used for performing amplifications. It is noted that these temperature profiles are merely exemplary and that different temperature profiles may also be used.

As illustrated in FIG. 3A, after the denaturation of the sample, the oligonucleotides are allowed to anneal to the target at a low temperature. The annealing temperature is then gradually increased until the optimum temperature for the polymerase is reached.

FIG. 3B illustrates another temperature profile for performing an amplification. As illustrated, the annealing temperature is raised by a combination of gradual rises in temperature with temperature plateaus for a period of time.

FIG. 3C. illustrates yet another temperature profile for performing an amplification. As illustrated, the annealing temperature is raised in a step-wise manner. As also illustrated, the incubation time after each ramp/step is shorter than previous one. This ramping approach is contemplated to increase the stringency of apposition annealing of the oligonucleotide to the target sequence, thereby limiting the formation of concatamers, i.e. tandem repeats of the target sequence or the primers.

It is noted that polymerase activity is generally temperature dependent. More specifically, a polymerase will have a maximum level of activity at a certain temperature, that activity decreases as the temperature increases or decreases from the optimal temperature. Given that the amplification is conducted over a range of temperatures, it may be desirable to utilize multiple polymerases where different polymerases are used at different temperatures. For example, a polymerase with optimum activity at a lower temperature (e.g. about 37° C.) can be added into the mixture at the annealing step to enhance extension of the annealed oligonucleotides at low temperatures. Examples of such polymerases include, but are not limited to, the large proteolytic fragment of the DNA polymerase I of the bacterium *E. coli*, commonly known as Klenow polymerase, *E. coli* DNA polymerase 1, and bacteriophage T7 DNA polymerase.

Given that multiple cycles of amplification are needed in order to perform the methods of the present invention, it is preferred to use a thermostable polymerase, such as TAQ DNA polymerase derived from the thermophilic bacterium *Thermus aquaticus*, as well as various commercially available high or low fidelity thermostable polymerases such as ACCUTAQ and KLENTAQ from Sigma.

Thermostable polymerases are typically most active at higher temperatures. Hence, in order to extend the oligonucleotides at lower temperatures, it is necessary to incubate the sample at the lower temperatures for a longer period of time than at higher temperatures. This feature is illustrated in FIGS. 3A–C. where the slope of the temperature curve is smaller at lower temperatures than at higher temperatures.

It may be necessary to provide the amplification mixture a sufficient amount of salts such as $Mg^{2+}$, KCl and NaCl, or polyethylene glycol ("PEG"). Cations such as $Mg^{2+}$, $K^+$ and $Na^+$ are believed to bind to DNA and enhance the stability of duplexes. Polymers such as PEG is believed to increase the condensation of DNA and favor the formation of DNA complexes between strands. For example, extra $Mg^{2+}$ may be added to the amplification mixture at a concentration between zero and 100 mM (assuming $Mg^{2+}$ is provided in the polymerase reaction buffer), preferably between 5 and 20 mM.

The amplification may also contain nucleoside triphosphate substrates such as dATP, dCTP, dGTP, dTTP, dITP, ATP, CTP, GTP, UTP in sufficient quantities to support the degree of amplification desired. The amount of deoxyribonucleotide triphosphates substrate required for substantial DNA amplification by primer extension polymerase amplification may be in the range of 50 to 500 mM, preferably in the range of 100 to 300 mM. Optionally, nucleoside triphosphate analogues may be substituted or added to the above mixture, provided that the base pairing, polymerase, and strand displacing functions are not adversely affected to the point that the amplification does not proceed to the desired extent.

5. Isolation and Characterization of Mutagenized Polynucleotides

The library of mutagenized polynucleotides formed after multiple amplification cycles may be analyzed or characterized by using any of a variety of methods well known in the art. For example, the library may be sequenced, restriction digested, electrophoresed, or hybridized against a reference nucleic acid molecules. In one embodiment, the amplification reaction mixture is subjected to agarose gel electrophoresis, stained with DNA binding dyes such as ethidium bromide, the amplification product may appear as a "smear" or "cloud" under UV light, representing randomly mutagenized target sequences.

The mutagenized polynucleotides may be isolated from the amplification products by using methods known in the art, such as gel eletrophoresis, gel filtration, ion exchange chromatography, affinity chromatography and magnetic beads. The isolated DNA may be digested with restriction enzymes on the sites that are carried by the first and second primers and incorporated into the mutagenized target sequence to yield fragments suitable for subcloning into a vector. The vector used for cloning may not be critical so long as the DNA fragment can be ligated into the vector. Alternatively, the isolated DNA may be directly subcloned into a vector by using the commercially available cloning kits (e.g. TA cloning kits from Invitrogen). Each clone may be sequenced by using conventional dideoxynucleotide sequencing method or by using an automatic sequencer.

6. Expression of Mutagenized Polynucleotides

The mutagenized polynucleotides may also be cloned into expression vectors that comprise transcription and translation signals next to the site of insertion of the polynucleotides to allow expression of the polynucleotides in host cells. Alternatively, the mutagenized polynucleotides may carry transcription and translation initiation and termination signals that control the expression.

The host cells for expression of the mutagenized polynucleotides may be prokaryotic and eukaryotic cells. Examples of prokaryotic cells include but are not limited to those of bacterial cell types, both gram-negative and gram-positive, such as Escherichia coli, Bacillus, Penicillium, Streptomycetes and Salmonella. Examples of eukaryotic cells include but are not limited to yeast, algae, fungi, plant, insect, mammalian (e.g. mouse, hamster, primate, human) cells, both cell lines and primary cultures. Plant cells include maize, rice, wheat, cotton, soybean, sugarcane, tobacco, and arabidopsis. Mammalian cells include stem cells, including embryonic stem cells, zygotes, fibroblasts, lymphocytes, kidney, liver, muscle, and skin cells.

The choice of host cell for expression of the mutagenized polynucleotides depends on several factors including the molecular characteristic of the mutant to be screened. For example, if the mutant protein expressed confer resistance to certain antibiotics, the host cell may be a suitable bacterial cell. If the mutant protein expressed confer resistance to apoptosis (programmed cell death), a mammalian cell may be an appropriate choice for the host cell.

7. Screening of Mutagenized Polypeptides

The mutant protein may be selected by using various methods, depending on its desired function. Selection may be achieved by using a selectable marker, easily assayed enzymes such as beta-galactosidase, luciferase, chloramphenicol acetyl transferase and secreted embryonic alkaline phosphatase; proteins for which immunoassays are readily available such as hormones and cytokines; proteins which confer a selective growth advantage on cells such as adenosine deaminase, aminoglycoside phosphotransferase, thymidine kinase, xanthine-guanine phosphoribosyltransferase (XGPRT), and proteins which provide a biosynthetic capability missing from an auxotroph; proteins which confer a growth disadvantage on cells, for example enzymes that convert non-toxic substrates to toxic products such as thymidine kinase (when used with medium containing bromodeoxyuridine) and orotidine-5'-phosphate decarboxylase (when used with 5-fluoroorotic acid); and proteins which are toxic such as ricin, cholera toxin or diphtheria toxin. Screening can also be done by observing such aspects of growth as colony size, halo formation, or by using automatic screening devices such as fluorescence activated cell sorter (FACS) and automatic ELISA.

In addition, screening for desired affinity to a ligand may be accomplished by binding to an affinity column or a solid support. Hydrolytic enzymes (e.g. proteases, amylases) can be screened by including the substrate in an agar plate and scoring for a hydrolytic clear zone or by using a calorimetric indicator (Steele et al., Ann. Rev. Microbiol. (1991) 45: 89–106).

A phage display system may also be used to screen for mutant protein with desired function. The mutagenized target sequences may be cloned into a phage DNA at a site which results in transcription of a fusion protein. The phage containing the recombinant DNA undergoes replication in bacterial cells. The leader sequence of the fusion protein directs the transport of the fusion protein to the tip of the phage particle. Thus the fusion protein which is particularly encoded by mutagenized target sequence is displayed on the phage particle for detection and selection by methods described above.

EXAMPLE

The gene encoding a penicillinase from *Bacillus licheniformis* was used as a target to be randomly mutagenized. By randomly mutating the enzyme, isozymes which show altered hydrolytic activity and/or specificity against various penicillins and cephalosporins may offer clues to 1) how antibiotics can be designed to thwart the inevitable evolution towards β-lactamases which render pathogenic bacteria resistant to drug therapy, and 2) offer further information for the study of protein structure-function relationships.

The gene encoding the *Bacillus licheniformis* was isolated from a plasmid pELB1. The plasmid pELB1 is a pBR322 derivative, containing the "exolarge" form of the *B. licheniformis* b-lactamase gene, utilizing the *Bacillus amyloliquefaciens* promoter and subtilisin signal sequence, and Bacillus and *E. coli* origins of replication (Ellerby, L. M., Escobar, W. A., Fink, A. L., Mitchinson C., Wells JA (1990) Biochemistry, Jun 19; 29(24):5797–806).

pELB1 was digested with restriction enzymes NdeI (incorporating the 'START' codon ATG) and DraIII, a site unique to the plasmid immediately downstream of the gene's TM (STOP) codon. This double-stranded polynucleotide fragment encodes a 273 amino acid β-lactamase.

5' and 3' primers for subsequent polymerase amplification that flank the polynucleotide fragment encodes a 273 amino acid β-lactamase were designed to incorporate the START and STOP codons, respectively. The 5' flanking primer includes a START codon and a sequence complementary to a 3' sequence of the sense strand of the polynucleotide fragment encoding the β-lactamase as described above. The 3' flanking primer includes a STOP codon and a sequence complementary to a 3' sequence of the antisense strand of the polynucleotide fragment encoding the β-lactamase as described above. The START and STOP codons were designed to be recognized in *E. coli* strain BL21(DE3). Examples of the 5'- and 3'-primers used are listed below.

SEQ. ID. NO. 1: 5'-primer having a NdeI site (underlined):

5'-CTTTAAGAAGGAGATATACATATGTCGCAACC-TGCCGAGAAGAATGAAAAG-3'

SEQ. ID. NO. 2: 3'-primer:

5'-GATATGAGCTTGATCACCAAGTGACTCTATTT-ATTTATTTGCCGTTCAT-3'

Amplifications of the β-lactamase gene were carried out, using synthesized oligonucleotides of 20 and 30 nucleotides in length in separate reactions, randomly incorporating either A,T,G, or C. nucleoside tri-phosphates at each position. These randomly sequenced oligonucleotides; specifically, the 20-mers and 30-mers, formed a library of oligonucleotides with various sequences which were used in subsequent amplifications designed to randomly mutate the β-lactamase gene template.

The amplifications were performed using a polymerase catalyzed primer extension. During the amplifications, the isolated β-lactamase gene template, the 5' and 3' flanking primers, and the randomized oligonucleotide library can interact and anneal with each other to form imperfect double-strand sequences. Several thermostable polymerases including Vent, Taq and Ultma (Perkin Elmer Co. Calif.) DNA polymerase were used under varying salt conditions, typically at 5 to 15 mM $MgCl_2$. Table I lists concentrations of various reagents for an exemplary amplification of the present invention.

A typical cycle of amplification was programmed to run as follows. In order to enhance annealing of the random oligonucleotides over the entire length of the gene template, and allow the annealing despite significant mismatches, low annealing temperatures were used initially (e.g. 40° C.), which were ramped upward to the optimum temperature of 72 ° C. for a typical thermastable DNA polymerase. Synthesis of polynucleotides via primer extensions was followed by denaturation at 90° C. Up to 45 cycles were employed to generate randomized products.

TABLE I

| Reagent | Volume (µL) | Final concentration (/100 µL) |
|---|---|---|
| Sterile $H_2O$ | 57.0 | N/A |
| Template | 1.0 | $10^2$–$10^4$ copies |
| 10× Polymerase Buffer | 10.0 | 1× |
| 50 mM $MgCl_2$ | 20.0 | 10.0 µM |
| 10 mM dATP | 2.0 | 200.0 µM |
| 10 mM dCTP | 2.0 | 200.0 µM |
| 10 mM dGTP | 2.0 | 200.0 µM |
| 10 mM dTTP | 2.0 | 200.0 µM |
| 5' Primer | 1.0 | 0.5 µM |
| 3' Primer | 1.0 | 0.5 µM |
| Random Oligonucleotides | 1.0 | 0.5 µM |
| DNA Polymerase (Ultma) | 1.0 | 1 U |

Figure 4:
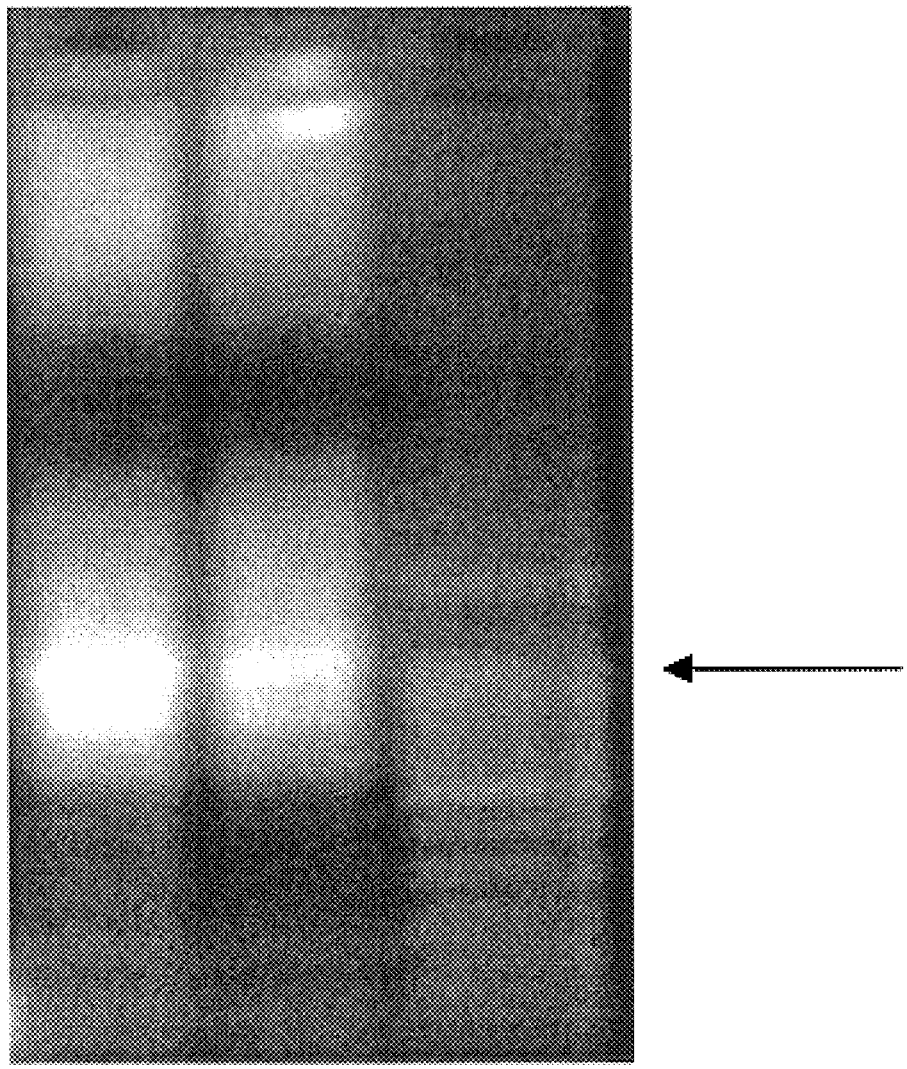
FIG. 4 illustrates mutagenesis reaction products separated by agarose gel. Lanes 1 and 2 correspond to reaction products as a resulting of utilizing 20 mer and 30 mer random oligonucleotides, respectively. Lane 3 corresponds to 100 bp DNA molecular weight marker.

The amplification products were separated using gel electrophoresis, stained with ethidium bromide, and visualized under UV light. The electrophoresed DNA products from the reactions including 20-mer and 30-mer random oligonucleotides appear as "smears" (FIG. 4, lanes 1 and 2, respectively ). Compared to the 100 bp. (base pairs) molecular weight marker shown in lane 3 of FIG. 4, the "smears" indicate that the amplified products vary in size, but exhibit the highest population at a position (indicated by an arrow) that correlates with the size of the original β-lactamase gene template (about 1000 bp. in length). This is indicative of expected random and multiple additive insertions and/or deletions, leading to amplification products of varying lengths.

Figure 5:
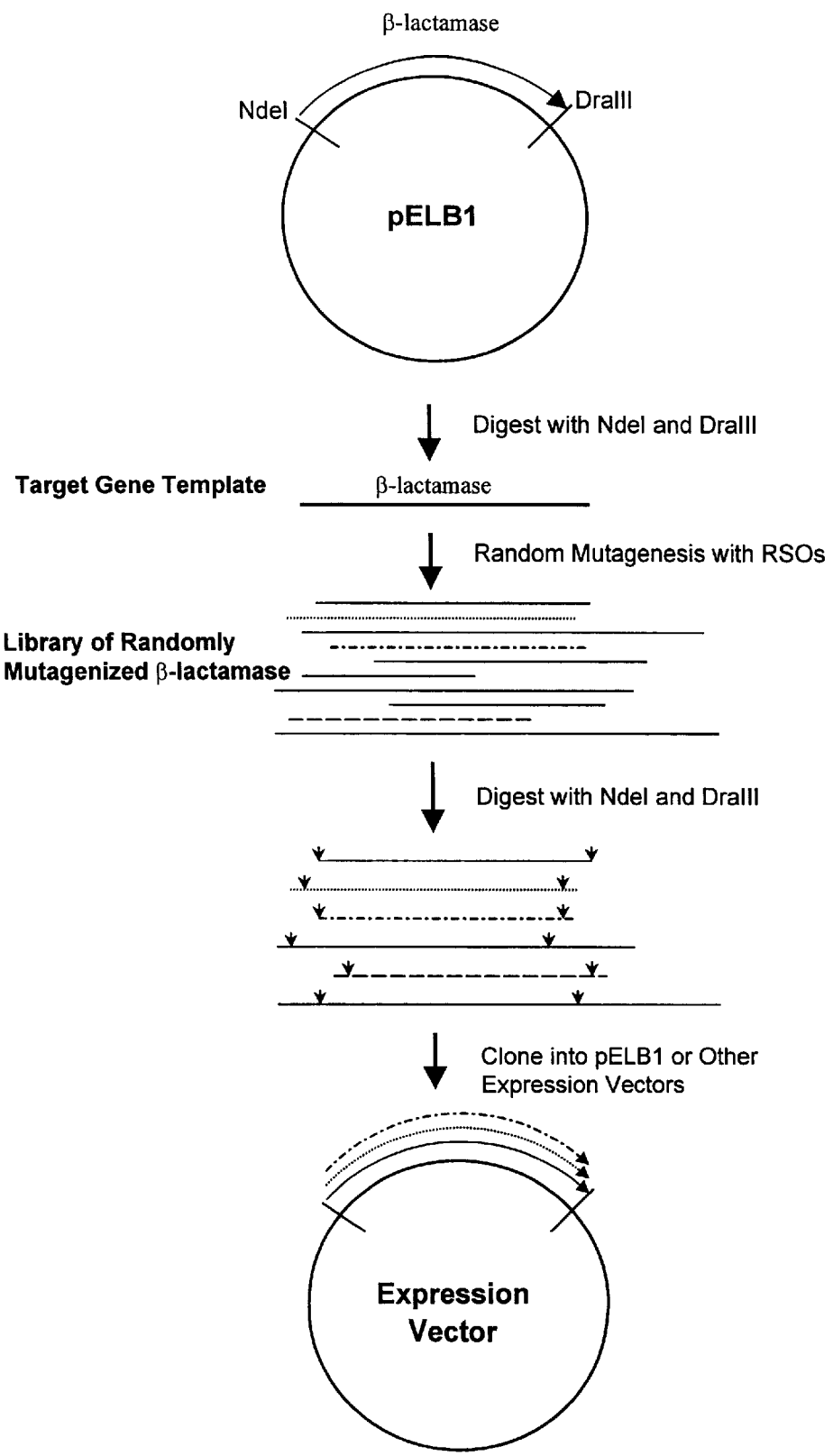
FIG. 5 schematically illustrates subcloning of a library of randomly mutagenized target gene sequences into a bacterial expression vector.

Amplification products are extracted from the gel by methods know to those of the art (or, e.g. Qiagen). The isolated DNA is digested with the NdeI and DraIII restriction endonucleases for efficient subsequent subcloning, and ligated (using a T4 DNA ligase) into a suitable expression vector (e.g. pELB2, FIG. 5). The products of the ligation reactions are used to transform *E. coli* host such as strain BL21(DE3) (FIG. 5).

Transformant constructs containing encoded polypeptides which confer desired characteristics to the host cells to be able to proliferate under specified conditions can be isolated and purified. Specific changes which result in the appearance of desired characteristics can be identified by sequence analysis of the selected construct(s).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the claims.

What is claimed is:

1. A method for producing a library of mutagenized polynucleotides from a target sequence comprising:
  forming a sample comprising
    (i) a target sequence including a section to be mutagenized,
    (ii) a first primer including a sequence complementary to a 3' sequence of a sense strand of the section of the target sequence,
    (iii) a second primer including a sequence complementary to a 3' sequence of an antisense strand of the section of the target sequence, and
    (iv) a library of oligonucleotides; and
  performing multiple cycles of primer extension amplification on the sample using a polymerase where primer extension is performed under conditions suitable for the first and second primers to be extended and for the oligonucleotides to anneal to a portion of the target sequence or amplification products thereof which the oligonucleotides are not known to anneal to form an imperfect double-stranded sequence and be extended by the polymerase;
  wherein a library of mutagenized polynucleotides are produced as amplification products of the multiple amplification cycles.

2. The method according to claim 1 wherein the first and second primers include at least one restriction site.

3. The method according to claim 1 wherein one of the first and second primers includes an ATG or an GTA sequence and the other primer includes a sequence encoding a translation stop codon.

4. The method according to claim 1 wherein the lengths of the first and second primers is between 10 and 80 nucleotides.

5. The method according to claim 1 wherein the at least one oligonucleotide has a length between 15 and 30 nucleotides.

6. The method according to claim 1 wherein at least a portion of the multiple cycles of primer extension polymerase amplification is performed such that extension by the polymerase is at least partially performed at a temperature below 70° C. for at least 30 sec.

7. The method according to claim 1 wherein at least a portion of the multiple cycles of primer extension polymerase amplification is performed such that extension by the polymerase is at least partially performed at a temperature below 60° C. for at least 30 sec.

8. The method according to claim 1 wherein at least a portion of the multiple cycles of primer extension polymerase amplification is performed such that extension by the polymerase is at least partially performed at a temperature below 50° C. for at least 30 sec.

9. The method according to claim 1 wherein at least a portion of the multiple cycles of primer extension polymerase amplification is performed such that extension by the polymerase is at least partially performed by heating the amplification reaction mixture from temperature of between 30° C. to 50° C. to a temperature between 65° C. to 75° C. over the course of at least 30 sec.

10. The method according to claim 1 wherein the imperfect double-stranded sequence includes a bulge.

11. The method according to claim 1 wherein the imperfect double-stranded sequence includes a loop.

12. The method according to claim 1 wherein the library of mutagenized polynucleotides formed may include homologs of the target sequence where at least two sequences from the oligonucleotides have been inserted.

13. The method according to claim 1 wherein the mutagenized polynucleotides formed may include homologs of the target sequence where at least two portions of the target sequence have been deleted.

14. The method according to claim 1 wherein the mutagenized polynucleotides includes sequences that have been mutagenized at at least two separate locations relative to the target sequence.

15. The method according to claim 1 wherein the oligonucleotides In the library Include a portion which is complementary to the target sequence and a portion which is not complementary to the target sequence relative to where the oligonucleotide anneals to the target sequence during primer extension amplification.

16. The method according to claim 1 wherein the at least one oligonucleotide has a length between 10 and 80 nucleotides.

17. The method according to claim 1 wherein the at least one oligonucleotide has a length between 10 and 50 nucleotides.

18. The method according to claim 1 wherein at least a portion of the multiple cycles of primer extension polymerase amplification is performed such that extension by the polymerase is at least partially performed at a temperature below 55° C. for at least 30 sec.

19. The method according to claim 1 wherein the library of mutagenized polynucleotides formed may include homologs of the target sequence where at least two sequences have been inserted or deleted.

20. The method according to claim 1 wherein the mutagenized polynucleotides includes sequences that have been mutagenized at at least two separate locations relative to the target sequence.

21. A method for producing a library of mutagenized polynucleotides from a double-stranded target sequence, comprising:
(a) forming a sample comprising
 (i) a target sequence having sense and antisense strands and including a section to be mutagenized,
 (ii) a first primer including a sequence complementary to a 3' sequence of the section of the sense strand of the target sequence,
 (iii) a second primer including a sequence complementary to a 3' sequence of the section of the antisense strand of the target sequence, and
 (iv) a library of oligonucleotides;
(b) performing multiple cycles of primer extension amplification on the sample in the presence of at least one polymerase such that at least one of the oligonucleotides anneals to a portion of the section of either the sense or antisense strand of the target sequence which the oligonucleotide is not known to anneal to form an imperfect double-stranded sequence and is extended by the polymerase, and a mutagenized double-stranded polynucleotide is formed comprising sequences of the first and second primers and the sequence of the extended oligonucleotide.

22. The method according to claim 21 wherein the oligonucleotides in the library include a portion which is complementary to the target sequence and a portion which is not complementary to the target sequence relative to where the oligonucleotide anneals to the target sequence during primer extension amplification.

23. The method according to claim 21 wherein the at least one oligonucleotide has a length between 10 and 80 nucleotides.

24. The method according to claim 21 wherein the at least one oligonucleotide has a length between 10 and 50 nucleotides.

25. The method according to claim 21 wherein at least a portion of the multiple cycles of primer extension polymerase amplification is performed such that extension by the polymerase is at least partially performed at a temperature below 55° C. for at least 30 sec.

26. The method according to claim 21 wherein the library of mutagenized polynucleotides formed may include homologs of the target sequence where at least two sequences have been inserted or deleted.

27. The method according to claim 21 wherein the mutagenized polynucleotides includes sequences that have been mutagenized at at least two separate locations relative to the target sequence.

* * * * *